United States Patent [19]

Harandi et al.

[11] Patent Number: 4,777,321

[45] Date of Patent: * Oct. 11, 1988

[54] FEEDSTOCK PREPARATION AND CONVERSION OF OXYGENATES TO OLEFINS

[75] Inventors: Mohsen N. Harandi, Lawrenceville; Hartley Owen, Belle Mead; Sean C. Smyth, Plainsboro, all of N.J.

[73] Assignee: Mobil Oil Corporation, New York, N.Y.

[*] Notice: The portion of the term of this patent subsequent to Nov. 22, 2004 has been disclaimed.

[21] Appl. No.: 43,716

[22] Filed: Apr. 29, 1987

[51] Int. Cl.[4] ............................................. C07C 1/20
[52] U.S. Cl. ...................................... 585/640; 203/14; 203/18; 585/408; 585/469; 585/639; 585/733
[58] Field of Search ............... 203/14, 18, DIG. 23; 585/640, 733, 465, 639, 408

[56] References Cited

U.S. PATENT DOCUMENTS

| | | | |
|---|---|---|---|
| 3,293,154 | 12/1966 | Newton | 203/18 |
| 4,014,667 | 3/1977 | Barker | 203/18 |
| 4,025,575 | 5/1977 | Chang et al. | 260/682 |
| 4,083,888 | 4/1978 | Caesar et al. | 585/640 |
| 4,349,415 | 9/1982 | DeFilippi et al. | 203/14 |
| 4,665,237 | 5/1987 | Arakawa et al. | 568/697 |
| 4,665,249 | 5/1987 | Mao et al. | 585/408 |

Primary Examiner—Curtis R. Davis
Attorney, Agent, or Firm—Alexander J. McKillop; Michael G. Gilman; L. G. Wise

[57] ABSTRACT

A process for converting crude aqueous methanol feedstock or the like to olefinic hydrocarbons in contact with a medium pore shape selective crystalline acid zeolite catalyst, wherein the improvement comprises contacting the aqueous methanol feedstock with a liquid propane-rich hydrocarbon extractant under liquid extraction conditions, recovering an aqueous phase containing the major amount of water introduced with the feedstock, recovering an organic extract phase comprising the hydrocarbon extractant and a portion of methanol introduced in the feedstock, and converting the extracted methanol at elevated temperature under catalytic reaction conditions to produce predominantly olefinic hydrocarbons.

9 Claims, 5 Drawing Sheets

FEEDSTOCK PREPARATION AND CONVERSION OF OXYGENATES TO OLEFINS

BACKGROUND OF THE INVENTION

This invention relates to techniques for converting an oxygenated aliphatic compound, such as methanol, to lower olefins. In particular, it provides a continuous process for producing an olefinic product rich in $C_2$-$C_5$ alkenes, especially $C_4^+$ alkenes. In view of the availability and low cost of synthetic methanol (MeOH), primary emphasis is placed on this feedstock material in following description of the methanol-to-olefin (MTO) process.

Processes for converting lower oxygenates such as methanol to hydrocarbons are known and have become of great interest in recent times because they offer an attractive way of producing liquid hydrocarbon fuels, especially gasoline, from sources which are not of liquid petroleum origin. In particular, they provide a way by which methanol can be converted to a major amount of $C_2$-$C_5$ olefins and a minor amount of gasoline boiling range products in good yields. The methanol, in turn, may be readily obtained from coal by gasification to synthesis gas and conversion of the synthesis gas to methanol by well-established industrial processes. As an alternative, the methanol may be obtained from natural gas by other conventional processes, such as steam reforming or partial oxidation to make the intermediate syngas. Crude methanol from such processes usually contain a significant amount of water, usually in the range of 4 to 20 wt. %; however, the present invention is useful for removing water in lesser amounts or greater.

Various zeolitic catalysts are useful for converting methanol and other lower aliphatic alcohols or corresponding ethers to olefins. Recent interest has been directed to a catalytic process for converting methanol over ZSM-5 and related catalysts to valuable hydrocarbons rich in ethene and $C_3^+$ alkenes. Various processes are described in U.S. Pat. Nos. 3,894,107 (Butter et al); 3,928,483; 4,025,575; 4,252,479 (Chang et al); 4,025,572 (Lago); 4,328,384 (Daviduk et al); and 4,547,616 (Avidan et al); incorporated herein by reference. It is generally known that MTO processes can be optimized to produce a major fraction of $C_2$-$C_4$ olefins; however, a significant $C_5^+$ byproduct may be coproduced. Prior process techniques for increasing lower olefin selectivity have provided for controlled deposition of coke byproduct on the catalyst surface.

Methanol may be first subjected to a dehydrating step, using a catalyst such as gamma-alumina, to form an equilibrium mixture of methanol, dimethyl ether (DME) and water. This mixture is then passed at elevated temperature and pressure over a catalyst such as ZSM-5 zeolite for conversion to the hydrocarbon products. Water may be removed from the methanol dehydration products prior to further conversion to hydrocarbons and the methanol can be recycled to the dehydration step, as described in U.S. Pat. No. 4,035,430. Removal of the water is desirable because the catalyst may tend to become deactivated by the presence of excess water vapor at the reaction temperatures employed; but this step is not essential.

Typically the crude methanol feestock employed in MTO processes contains about 4 to 20 wt. % water as the principal impurity. Excessive water not only contributes to catalyst deactivation, but also requires larger volume equipment to handle the increased throughput. Various proposals have been put forth for reducing the water content of crude methanol, for instance the distillation system described by Mao et al in copending U.S. patent application Ser. No. 823,153, filed Jan. 27, 1986, incorporated by reference.

It is main object of the present invention to provide a novel and economic technique for removing excess water from crude MTO feedstocks, including novel operating methods and equipment for treating these oxygenate feedstocks.

SUMMARY OF THE INVENTION

A continuous technique has been found for converting crude oxygenate feedstock, such as methanol and/or dimethylether, to predominantly olefinic hydrocarbons in a catalystic reaction zone with a crystalline acid zeolite catalyst at elevated temperature. Processes and apparatus are provided for contacting a crude oxygenate feedstock containing a minor amount of water with a liquid hydrocarbon extraction stream rich in propane and lighter hydrocarbons under extraction conditions favorable to selective extraction of the oxygenate, thereby providing an extract liquid stream rich in oxygenate and an aqueous raffinate stream lean in oxygenate. Substantially free of water, the extracted oxygenate is passed to the reaction zone under process conditions to convert oxygenate to predominantly olefinic hydrocarbons. This is followed by cooling reaction effluent to recover aqueous liquid byproduct, gas rich in $C_3^-$ hydrocarbons, and product comprising $C_4^+$ hydrocarbons. Extractant is provided by condensing and recycling at least a portion of the $C_3^-$ liquid phase for use as propane-rich extraction liquid. A major advantage of $C_3^-$ recycle is that an increased circulation of $C_3^-$ material through the reaction zone can provide reactant dilution and enhanced selectivity of $C_2$-$C_5$ olefins.

These and other objects and features of the invention will be understood from the following description and in the drawing.

DRAWING

FIG. 1 of the drawing is a schematic MTO process flowsheet depicting the present invention;

DETAILED DESCRIPTION

Suitable oxygenate feedstocks include $C_1$-$C_4$ aliphatic alcohols, ethers, aldehydes, ketones, etc. Dehydration mixtures of methanol and DME may contain about 10-60% DME, for instance.

Figure 1:
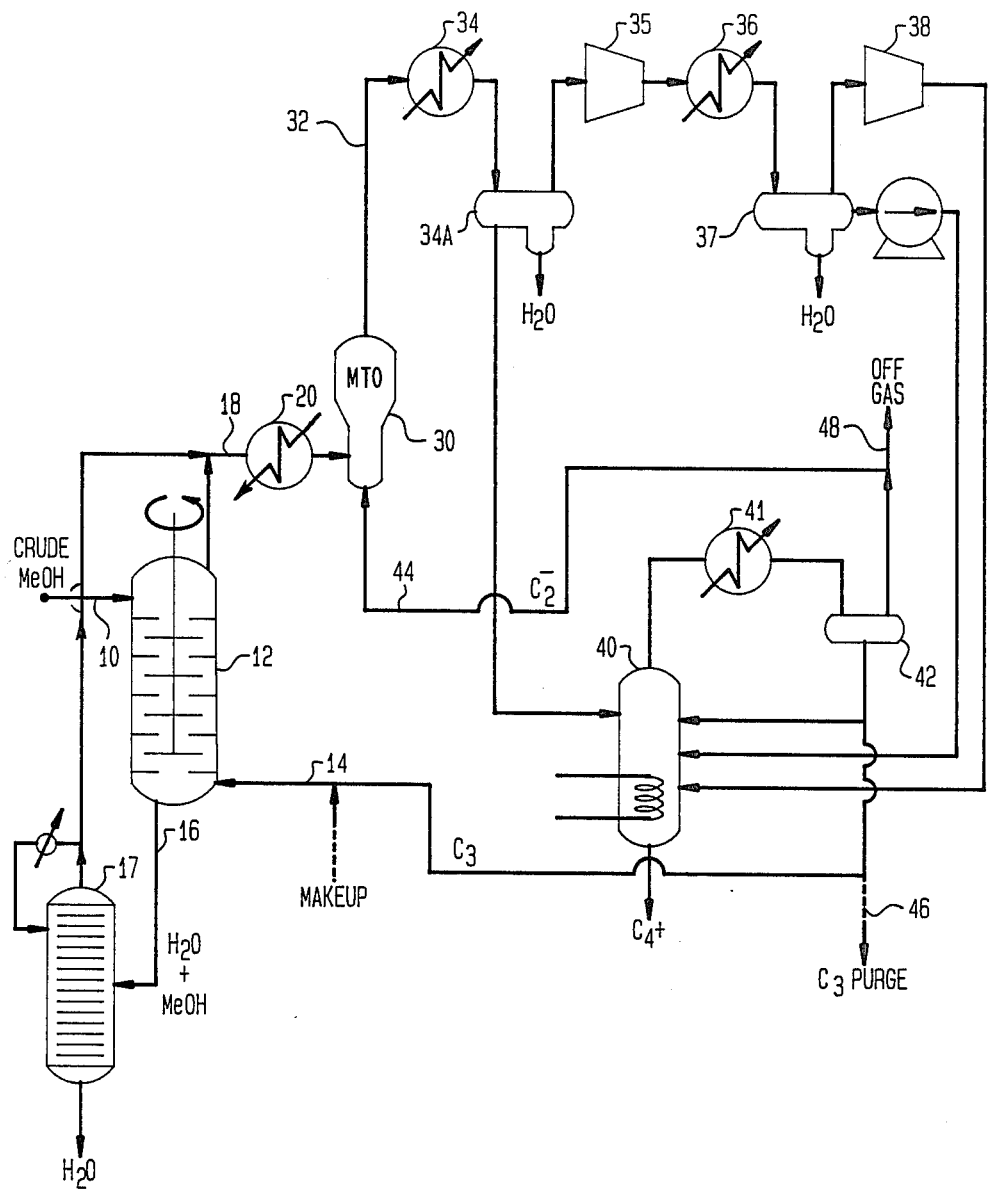

Referring to the FIG. 1 of drawing, crude methanol (MeOH) feedstock is introduced via conduit 10 to a top inlet of extraction unit 12, where it is contacted under liquid extraction conditions with a countercurrent stream of hydrocarbon liquid extractant introduced at a bottom inlet via conduit 14. An aqueous raffinate phase containing a major amount of the water present in the crude feedstock and a portion of MEOH is withdrawn via conduit 16. Raffinate methanol can be recovered in distillation tower 17 and combined with the extract phase in conduit 18. The lighter organic extract phase containing hydrocarbon extraction solvent and methanol is recovered from extraction unit 12 via conduit 18, passed through heat exchanger 20, and introduced at elevated temperature and process conditions suitable for conversion of substantially all of the methanol in contact with the MTO catalyst in reactor system 30. From the reactor system 30, the effluent product stream leaves via line 32 to a heat exchanger 34 and condensate accumulator 34A. Vapor is pressurized in primary compressor 35, cooled in intermediate condenser 36, and passed as a three-phase mixture to a primary phase separator 37 for recovery of byproduct water and condensed liquid. Secondary compressor 38 raises the vapor to suitable pressure (e.g.-1500–2200 kPa; 200–350 psig) for feeding to depropanizer tower 40 for recovery of $C_3^-$ gas overhead rich in $C_3$ hydrocarbons, especially propane and $C_2$–$C_3$ olefins for recycle. Advantageously, at least a portion of the $C_3$ tower overhead components is condensed by cooling with exchanger 41 and passed via accumulator 42 for use as reflux and liquid extractant. Propene contained in the $C_3$ liquid recycle stream can be further converted to $C_4^+$ hydrocarbons in reactor 30. Light gas 48 from the accumulator and optional $C_3^-$ purge stream 46 may be removed from the loop. A portion of ethene-rich overhead vapor may be recycled via line 44 directly to the MTO reactor 30 for further conversion.

This system configuration is particularly advantageous since it eliminates expensive cryogenic necessary for complete separtion of $C_2$–$C_3$ components. The $C_3^-$ purge stream 46 and ethene-rich offgas stream 48 may be utilized as fuel gas, or olefinic components can be further upgraded by oligomerization in a high severity reactor.

Tower bottoms comprise $C_4^+$ hydrocarbons, which may be further fractionated to recover isobutane or other components thereof. A recycle $C_3^-$ stream including at least a portion of liquid propane recovered from the process reactor effluent is sent via conduit 14 for use as extractant liquid, along with any added propane or other makeup hydrocarbon liquid added to the process extractant stream. The aqueous raffinate stream 16 consists essentially of water, partititioned methanol and a trace of hydrocarbon. This may be recovered and fractionated to provide a methanol-rich stream to be combined with crude feestock in conduit 10 or extract stream 18.

Separaton of $C_3-$ recycle from reactor effluent may be facilitated by employing an intermediate absorber unit (not shown) between the primary compressor and depropanizer tower for contacting compressed vapor with a liquid hydrocarbon sorption stream for selective sorption of $C_4+$ components.

EXTRACTION UNIT OPERATION

The preferred crude feedstock material is methanol containing about 4 to 17% by weight water. The extraction unit 12 is depicted as a stirred multi-stage vetical extracton column adapted for continuous operation at elevated pressure. Any suitable extraction equipment may be employed, including cocurrent, cross-current or single stage contactors, wherein the liquid methanol feedstock is intimately contacted with a substantially immiscible liquid hydrocarbon solvent, which may be a mixture of $C_3$–$C_4$ aliphatic components or relatively pure propane, butane, etc. This unit operation is described in *Kirk-Othmer Encyclopedia of Chemical Technology* (Third Ed.), 1980, pp. 672–721. Other equipment for extraction is disclosed in U.S. Pat. Nos. 4,349,415 (DeFilipi et al) and 4,626,415 (Tabak). The methanol extraction step can be performed advantageously in a countercurrent multistage design, such as a simple packed column, rotating disk column, agitated column with baffles or mesh, or a series of single stage mixers and settlers.

Figure 2:
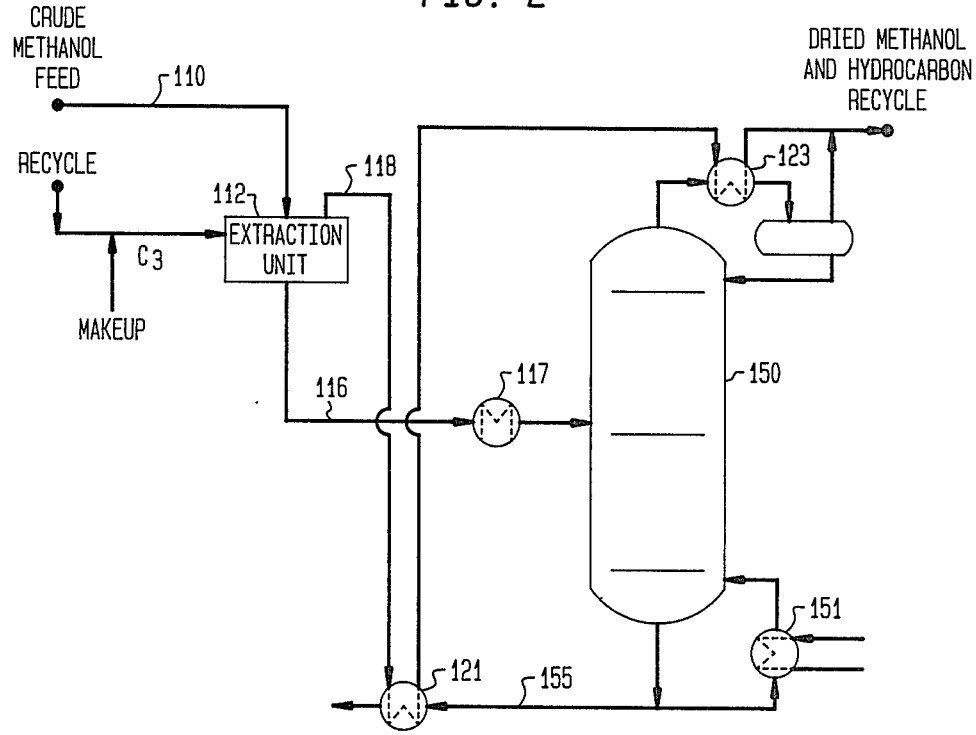
FIG. 2 is a flow diagram of the extraction and methanol dewatering subsystem for a preferred embodiment using $C_3$ aliphatic recycle.
Figure 3:
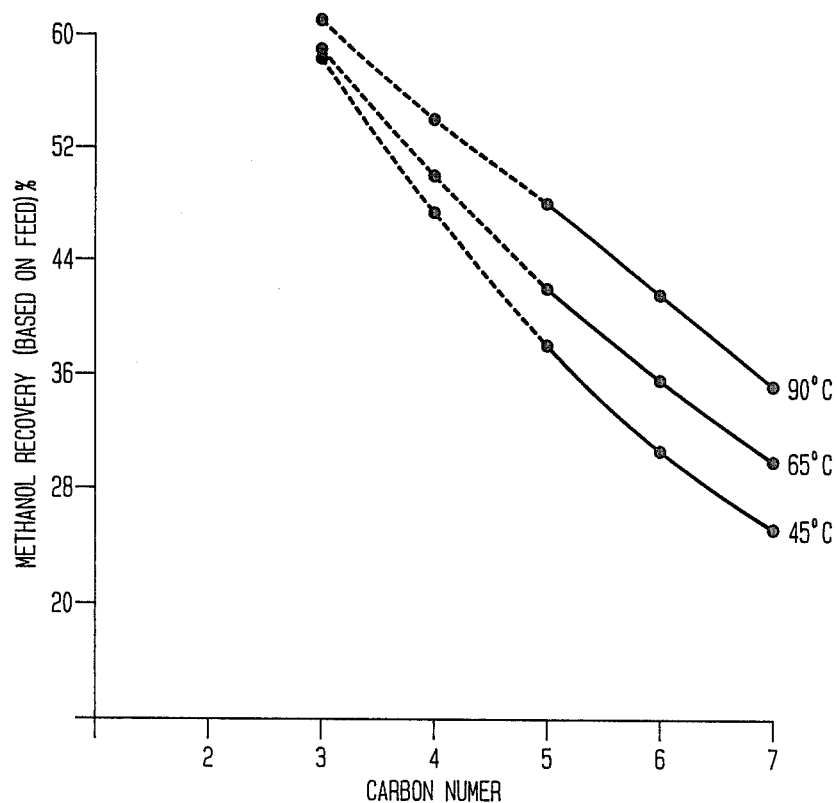
FIG. 3 is a graphic plot of methanol recovery vs. carbon number of n-alkane extractant, showing extraction temperature as parameter.
Figure 4:
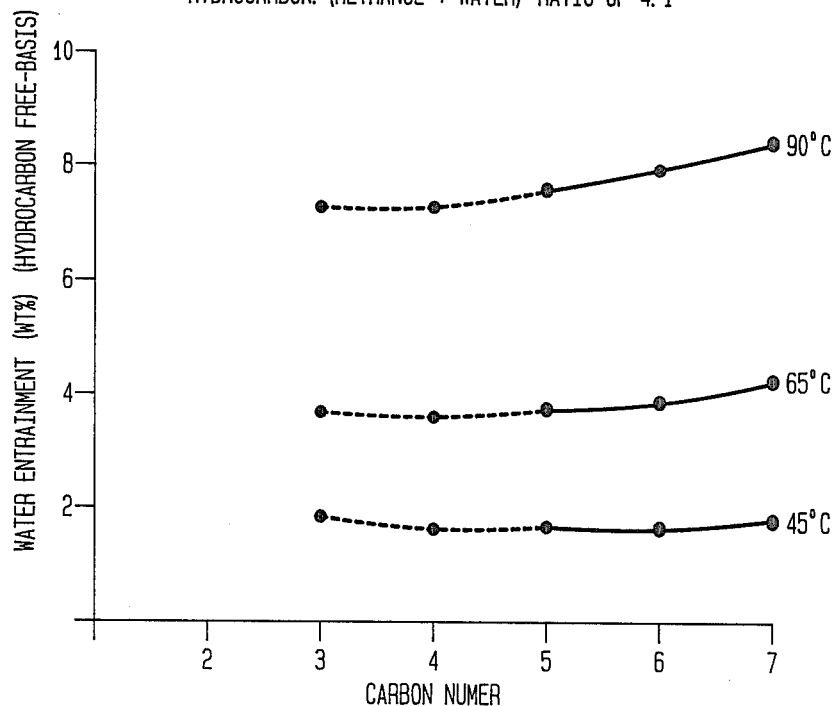
FIG. 4 is a corresponding graphic plot showing water entrainment in the extract phase for $C_3$-$C_7$ alkanes.

As an example of crude methanol dewatering technique, FIG. 2 shows an integrated extraction and distillation operation with thermal recovery, employing similar ordinal numbers for corresponding elements in FIG. 1. In this example crude methanol containing about 17 wt. % is fed via inlet 110 to extraction unit 112 at a flow rate of 16364 moles MeOH + 6080 moles $H_2O$, where it is contacted with 89776 moles of $C_3$ (propane) hydrocarbon at a temperature of 43° C. The extract phase containing 9596 moles of MeOH, 325 moles $H_2O$ (less than 2 wt. %), and 89560 moles $C_3$ hydrocarbon is passed via conduit 118, heat exchangers 121, 123 and combined with distilled methanol to provide a reactor system feedstream containing 16357, 1175 and 89776 moles, respectivlely. Raffinate stream 116, containing 6768 moles MeOH, 5755 moles $H_2O$, and 216 moles $C_3$ is heated in exchanger 117 and introduced to distillation tower 150 for further enrichment of the methanol overhead, which is condensed in exchanger 123 for reflux and reactor feed. Distillation bottoms are reboiled in exchanger 151 and a wastewater stream 155 is recovered containing about 4905 moles of water and 7 moles of MeOH.

MTO REACTOR SYSTEM

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, or Fe, within the zeolytic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

Catalyst versatility permits the same zeolite to be used in both methanol dehydration and olefin formation. While it is within the inventive concept to employ substantially different catalysts in plural stages, it is advantageous to employ a standard ZSM-5 having a silica alumina molar ratio of 70:1 or greater in a once-through fluidized bed unit to convert feedstock oxygenate to hydrocarbons.

The MTO catalysts preferred for use herein include the crystalline aluminosilicate zeolites having a silica to alumina ratio of at least 12, a constraint index of about 1 to 12. Representative of the ZSM-5 type zeolites are ZSM-5, ZSM-11, ZSM-12, ZSM-22, ZSM-23, ZSM-35, ZSM-38, and ZSM-48. ZSM-5 is disclosed and claimed in U.S. Pat. No. 3,702,886 and U.S. Pat. No. Re. 29,948;

ZSM-11 is disclosed and claimed in U.S. Pat. No. 3,709,979. Also, see U.S. Pat. No. 3,832,449 for ZSM-12; U.S. Pat. No. 4,076,979. Also, see U.S. Pat. No. 3,832,449 for ZSM-12; U.S. Pat. No. 4,076,842 for ZSM-23; U.S. Pat. No. 4,016,245 for ZSM-35; U.S. Pat. No. 4,046,839 for ZSM-38 and U.S. Pat. No. 4,375,573 for ZSM-48. The disclosures of all patents cited herein are incorporated herein by reference. The medium pore shape selective catalysts are sometimes known as porotectosilicates or "pentasil" catalysts, and may have a pore size of about 5 to 7 Angstroms.

Other catalysts and processes suitable for converting methanol/DME to lower olefins are disclosed in U.S. Pats. Nos. 4,393,265 and 4,613,720 (Bonifaz), U.S. Pat. No. 4,387,263 (Vogt et al) and European Patent Application Publ. No. 0081683 (Marosi et al). ZSM-34 and ZSM-45 are known MTO catalysts, as disclosed in U.S. Pat. No. 4,086,186 (Rubin et al) and European Patent Application No. 83305747.4 (Rosinski et al), respectively. In addition to the preferred aluminosilicates, silicoaluminophosphate, gallosilicate, borosilicate, ferrosilicate and "silicalite" materials may be employed.

ZSM-5 type pentasil zeolites are particularly useful in the MTO process because of their regenerability, long life and stability under the extreme conditions of MTO operations. Usually the zeolite crystals have a crystal size from about 0.02 to 2 microns or more, with large crystals on the order of 0.1-1 micron being preferred. In order to obtain the desired particle size for fluidization in the turbulent regime, the zeolite catalyst crystals are bound with a suitable inorganic oxide, such as silica, alumina, etc. to provide a zeolite concentration of about 5 to 90 wt. %. It is advantageous to employ a particle size range consisting essentially of 1 to 150 microns. Average particle size is usually about 20 to 100 microns, preferably 40 to 80 microns. The catalyst in the fluidized bed reactor is maintained at an average acid cracking activity (alpha value) of about 1 to 15, preferably about 3 to 8, on a coke-free basis. The average coke content is less than 15 weight percent, preferably about 5-10 wt. % of the clean-burned catalyst. By controlling the catalytic properties of the system, the selectivity to produce $C_2$-$C_5$ olefins can be enhanced.

MTO conversion in the presence of lower aliphatic diluents is described in U.S. Pat. No. 4,025,575 (Chang et) and in copending application Ser. No. 814,426 filed Dec. 30, 1985 (Kaeding), incorporated herein by reference. In the following example H-ZSM-5, prepared according to U.S. Pat. No. 4,375,458 (Dwyer) is modified to deposit MgO(5.1% Mg) into the pores.

EXAMPLE 1

Dewatered methanol is converted over the Mg-modified H-ZSM-5 at about 350° C. and 100 kPa in the presence of propane at a molar ratio of 3.1 $C_3$:MeOH, with methanol space velocity of about 0.4 WHSV. Under these conditions MeOH conversion is 100%, while a small amount of propane is produced. The $C_2$-$C_4$ olefins selectivity is about 61 wt. % in addition to about 29% butane and 5% $C_5$+ liquid product.

EXAMPLE 2

Comparison is made between a fluidized bed reactor operation with and without $C_3$ recycle. The data in Table 1 are directed to continuous conversion of dewatered methanol employing a particulate 25% HZSM-5 catalyst having an acid cracking value of 4 under steady state conditions, as described in U.S. Pat. No. 4,547,616 (Avidan et al), with recovery and recycle of ethene.

TABLE 1

| FLUIDIZED BED MTO REACTOR NET YIELDS | | |
|---|---|---|
| Component | Without Propane Diluent Yield (wt. %) | With Propane 3:1 Diluent Yield (wt. %) |
| Methane | 2.5 | 1.0 |
| Ethane | 2.4 | 0.9 |
| Ethene | — | — |
| Propane | 4.4 | 2.3* |
| Propene | 26.1 | 16.1 |
| Isobutane | 5.7 | 24.8 |
| N—butane | 1.7 | 7.3 |
| Butenes | 16.6 | 37.9 |
| Pentenes | 8.0 | |
| Hexenes | 2.0 | |
| Heptenes | 1.3 | |
| Octenes | 0.6 | |
| $C_5$ + (P + N) | 15.3 | 5.9 |
| $C_6$-$C_8$ (Aromatics) | 7.7 | 3.8 |
| $C_9$ + (Arom) | 5.7 | — |
| Total | 100.0 | 100.0 |

*net increase

Fuel gas make decreases by 4 wt. %; and isobutane product increases by about 19 wt. % in the case using 3 moles of propane diluent per mole of MeOH. Propane dilution appears to concentrate olefin production in the propane to butene range (ethene is recycled to extinction); while reducing fuel gas make and increasing isobutane production.

For cases involving the use of the propane diluent, the possibility of using a fixed bed reactor vs. a fluidized bed reactor should be considered. If the propane is recycled for improved selectivity, it will also help to control the temperature gradient across a fixed bed adiabatic reactor.

In a preferred embodiment, extracted methanol is passed to the reactor system with hydrocarbon extractant containing recycle. The combined feedstock and recycle is conducted at a temperature of about 275°-525° C., preferrably about 475°-500° C., and a pressure of about 100-1000 kPa to the MTO catalytic reactor. Effluent from the reaction zone is passed to a heat exchange condenser system and then to a separation zone without excessive loss of pressure. At high propane recycle ratio operation the reactor effluent remains in vapor phase after cooling, and the entire stream is compressed. At low propane recycle ratio the effluent stream may be partitioned into three streams in the separation zone. Typically, the separator is operated at conditions of about 38° C. (100° F.) and about 100-500 kPa (15-70 psia). The operation of the MTO unit is at low pressures and the effluent should be compressed for further processing. The increase in compression requirements and reactor size are the two process conditions most affected by the use of the propane diluent.

The $C_3^-$ recycle stream may comprise, on a molar basis, 25 to 90% of the reactor feedstream, preferably 35 to 80 mole %, preferably including propane in a molar ratio to neat methanol of about 0.5 to 4:1. It may be desirable to further fractionate the $C_3^-$ to recover and/or alkylate the isobutylene (see U.S. Pat. No. 4,633,028, Owen et al) or to upgrade olefins (see U.S. Pat. No. 4,579,999, Gould et al). Similarly, isobutane produced by oxygenate conversion or from other aliphatics may be separated for other use. Where a supply of outside propane is available, a major amount of the extractant can be comprised of recycled and makeup propane. Typically, about 95% of recycle are $C_2$-$C_3$ aliphaitic hydrocarbons.

Figure 5:
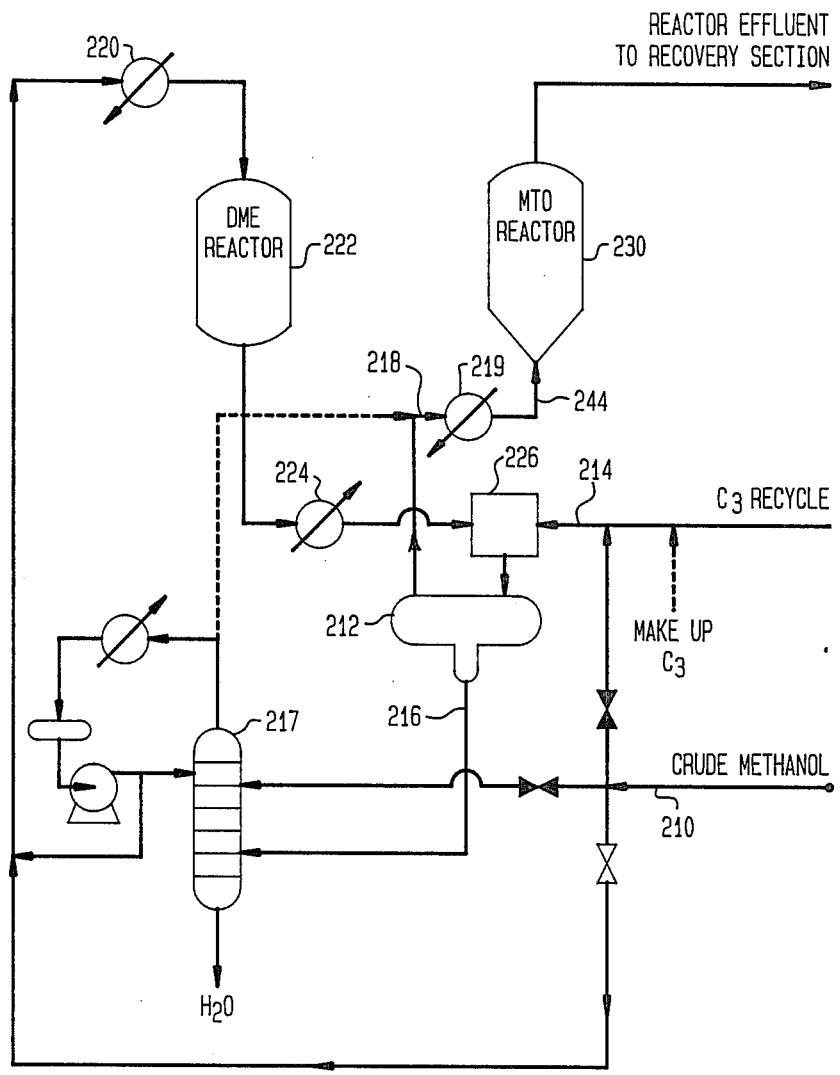
FIG. 5 is a process flow diagram for an alternative technique for dewatering MeOH-DME mixtures.

In the alternative embodiment of FIG. 5 the crude methanol is partially converted to dimethyl ether (DME) by a dehydration reaction step to provide a mixture of MeOH, DME and $H_2O$ prior to dewatering. Crude methanol introduced via line 210 may be fed directly to the DME reactor 222 or to the extraction unit via line 214 or fed to methanol recovery tower 217 along with aqueous raffinate stream 216. MeOH-rich overhead from tower 217 is heated in exchanger 220 and contacted with gamma-alumina or other acid metal oxide dehydration catalyst in DME reactor 222 to provide an intermediate aqueous MeOH-DME oxygenate mixture, which is cooled by exchanger 224 and mixed with liquid hydrocarbon extractant (e.g.-$C_3$ aliphatics) in a stirred mixing vessel 226 to effect thorough mixing of the oxygenate and hydrocarbon phaser. This liquid mixture is separated in phase separator unit 212 to provide an aqueous raffinate 216 and oxygenate-rich extract phase 218. After heating in exchanger 219, this mixture is passed via line 244 to the MTO reactor unit 230 for conversion of the oxygenates to lower olefins. The MTO reactor effluent is processed as in FIG. 1 to recover product and recycle streams.

While the invention has been described by examples, there is no intent to limit the inventive concept except as set forth in the following claims.

What is claimed is:

1. A continuous process for converting crude methanol to olefinic hydrocarbons in a catalytic reaction zone with a crystalline acid zeolite catalyst at elevated temperature comprising the steps of:
   (a) contacting a crude methanol feedstock containing a minor amount of water with a liquid hydrocarbon extraction stream rich in propane and lighter hydrocarbons under extraction conditions favorable to selective extraction of the methanol, thereby providing an extract liquid stream rich in methanol and an aqueous raffinate stream lean in methanol;
   (b) charging the extracted methanol substantially free of water to said catalytic reaction zone under process conditions for converting methanol to predominantly $C_2$-$C_5$ olefinic hydrocarbons;
   (c) cooling reaction effluent to recover aqueous liquid byproduct, gas rich in $C_3^-$ hydrocarbons, and product comprising $C_4^+$ hydrocarbons; and
   (d) condensing and recycling at least a portion of the $C_3^-$ liquid phase to step (a) for use as propane-rich extraction liquid.

2. The process of claim 1 wherein the MTO catalyst consists essentially of ZSM-5 type zeolite.

3. The process of claim 1 wherein the feedstock consists essentially of methanol and about 4 to 20 wt. % water, and wherein the extraction liquid comprises a major amount of $C_3$ hydrocarbon.

4. The process of claim 1 wherein a major amount of $C_3^-$ hydrocarbons from the reaction effluent are recycled with extracted methanol to the reaction zone as a vapor stream.

5. In the process for converting crude aqueous oxygenated hydrocarbon feedstock to olefinic hydrocarbons in contact with a medium pore shape selective crystalline acid zeolite catalyst;

the improvement which comprises:
   contacting the aqueous oxygenate feedstock with a liquid propane-rich hydrocarbon extractant under liquid extraction conditions;
   recovering an aqueous phase containing the major amount of water introduced with the feedstock;
   recovering an organic extract phase comprising the hydrocarbon extractant and a portion of oxygenate introduced in the feedstock;
   converting the extracted oxygenate at elevated temperature under catalytic reaction conditions to produce predominantly olefinic hydrocarbons rich in propene and butenes; and
   recovering $C_3^-$ hydrocarbons from conversion reaction effluent to provide recycle rich in propane and propene as liquid extractant.

6. The process of claim 5 wherein feedstock methanol is converted with a dehydration catalyst to provide an aqueous oxygenate feedstock containing methanol, dimethyl ether and water.

7. A process for converting crude aqueous methanol feedstock to predominantly $C_4^+$ olefin hydrocarbons in contact with a medium pore shape selective crystalline acid zeolite catalyst;

comprising the steps of:
   contacting the aqueous methanol feedstock with a propane-rich liquid hydrocarbon extractant comprising $C_3$ and lighter hydrocarbons under liquid extraction conditions;
   recovering an aqueous raffinate phase containing the major amount of water and a portion of methanol introduced with the feedstock;
   separating residual methanol from the raffinate phase for conversion;
   recovering an organic extract phase comprising the hydrocarbon extractant and a portion of methanol introduced in the feedstock;
   heating substantially the entire extract phase and the residual methanol from raffinate to provide a reactant stream comprising hot methanol and light propane-rich hydrocarbon vapor;
   converting the extracted methanol and residual methanol from the raffinate in the presence of the light hydrocarbon vapor at elevated temperature under catalytic reaction conditions to produce predominantly olefinic hydrocarbons;
   separating conversion reaction effluent to recover $C_4^+$ olefin-rich product, $C_3^-$ light gas, and water byproduct; and
   condensing and recycling at least a portion of the $C_3^-$ hydrocarbon components recovered from reaction effluent as extractant.

8. The process of claim 7 wherein the extraction step is conducted in a continuous extraction unit having means for contacting the extractant and feedstock under continuous conditions.

9. The process of claim 7 wherein the catalyst consists essentially of HZSM-5 and wherein the crude feedstock contains about 4 to 20 wt. % water, and about 10 to 60 wt. % dimethyl ether.

* * * * *